United States Patent [19]

Nair

[11] Patent Number: 5,703,062
[45] Date of Patent: Dec. 30, 1997

US005703062A

[54] N-HET-SUBSTITUTED GLYCEROPHOSPHOETHANOLAMINES

[75] Inventor: Haridasan K. Nair, Madison, Wis.

[73] Assignee: Clarion Pharmaceuticals Inc., Madison, Wis.

[21] Appl. No.: 749,511

[22] Filed: Nov. 15, 1996

Related U.S. Application Data

[60] Provisional application No. 60/008,314 Dec. 7, 1995.
[51] Int. Cl.⁶ ............................................. A61K 31/685
[52] U.S. Cl. ....................................................... 514/77
[58] Field of Search .................................................. 514/77

[56] References Cited

U.S. PATENT DOCUMENTS

| | | | |
|---|---|---|---|
| 4,372,949 | 2/1983 | Kodama et al. | 424/199 |
| 4,650,791 | 3/1987 | Nomura et al. | 514/82 |
| 5,116,992 | 5/1992 | Braquet et al. | 514/77 |

FOREIGN PATENT DOCUMENTS

| | | | |
|---|---|---|---|
| 2111-781-A | 4/1990 | Japan | 548/112 |

OTHER PUBLICATIONS

Andreesen, R., "Ether Lipids in the Therapy of Cancer," *Prog. Biochem. Pharmacol.*, vol. 22, pp. 118–131 (Kaeger, Basal 1988).

Brachwitz et al., *Chemistry and Physics of Lipids*, vol. 31, pp. 33–52 (1982).

*Cell*, vol. 15, pp. 261–267 (1978).

Chu–Moyer et al., *J. Org. Chem.*, vol. 60, pp. 5721–5725 (1995).

Clapp et al., *J. Heterocyclic Chem.*, pp. 107–108 (1968).

Handley, Dean A., Pharmacological Methods in the Controlled Information, pp. 23–58 (1989).

Hermetter, A. amd Paltauf, F., Procedures for the Synthesis of Ether Lipids, in H.K. Mangold and F. Paltauf, *Ether Lipids*, Academic Press (1983), p. 393 et.seq.

*J. Immunology*, vol. 119, pp. 950–954 (1977).

Koltai et al., *Drugs*, vol. 42, pp. 9–29 (1991).

Kunkel, S.L., "Inflammatory Cytokines, " pp. 1–15 In *Manual of Vascular Mediators*, P.A. Ward, Editor, produced by the publishers of Hospital Practice.

Paltauf, F. and Hermetter, A., Methods Enzymol., vol. 197, pp. 134–149 (1991).

Paltauf, F., *Chem. Phys. Lipids*, vol. 74, pp. 101–139 (1994).

*Primary Examiner*—Robert Gerstl
*Attorney, Agent, or Firm*—DeWitt Ross & Stevens SC

[57] ABSTRACT

The present invention relates to novel, therapeutically active fatty alkyl and alkenyl ether glycerophosphoethanolamines bearing a heterocyclic ring substituent on the ethanolamine nitrogen, methods of using the compounds and pharmaceutically acceptable salts thereof, and pharmaceutical compositions containing same. The novel, therapeutically active compounds and salts of the invention possess anti-tumor, anti-psoriatic, anti-inflammatory, and PAF antagonistic activities.

29 Claims, 5 Drawing Sheets

N-HET-SUBSTITUTED GLYCEROPHOSPHOETHANOLAMINES

Priority is claimed to provisional patent application Ser. No. 60/008,314, filed Dec. 7, 1995.

FIELD OF THE INVENTION

The present invention relates to novel, therapeutically active fatty alkyl and alkenyl ether glycerophospholipids bearing a defined heterocyclic (Het) substituent on the ethanolamine nitrogen, pharmaceutically acceptable salts of these compounds, methods of using these compounds and salts, and pharmaceutical compositions containing same. The compounds and salts of the invention have been discovered to possess anti-tumor, anti-psoriatic, anti-inflammatory, and anti-asthma activities.

BACKGROUND OF THE INVENTION

Synthetic fatty alkyl and alkenyl ether glycerophospholipids with potential anti-tumor properties have been reported in the literature. See, for example, F. Paltauf, Chem. Phys. Lipids Vol. 74, pp. 101–139 (1994). The compound 1-O-octadecyl-2-O-methyl-sn-glycero-3-phosphocholine (ET 18-OCH$_3$) has markedly potent anti-tumor activity. See R. Andreesen, "Ether Lipids in the Therapy of Cancer," Prog. Biochem. Pharmacol. Vol. 22, pp. 118–131 (Karger, Basel 1988). Treatment of cancer with a fatty alkyl ether glycerophosphoethanolamine component is also disclosed in U.S. Pat. No. 4,372,949. Halo substituted cytostatic analogs are described by H. Brachwitz et al., Chemistry and Physics of Lipids Vol. 31, pp. 33–52 (1982). Glycerophospholipids bearing a $C_{10-24}$ alkyl ether substituent in the 1-position, a cyclic amido group in the 2-position, and a cyclic ammonio group as part of the phosphoethanolamino function in the 3-position of the glyceryl backbone are described in U.S. Pat. No. 4,650,791. Also disclosed in U.S. Pat. No. 4,650,791 are synthetic intermediates wherein the substituents are as described in the preceding sentence herein except that there is a hydroxyl group at the 3-position or hydroxyl groups at both the 1-position and the 3-position of the glyceryl backbone. Glycerophosphoethanolamines bearing a non-cyclic, substituted amino substituent in the 2-position and a lower $C_{1-5}$ alkyl ether substituent in the 1-position of the glyceryl backbone are disclosed in U.S. Pat. No. 5,116,992.

Applicants disclose for the first time herein that the novel fatty alkyl and alkenyl ether glycerophosphoethanolamines of the invention, which bear a defined heterocyclic (Het) substituent on the ethanolamine nitrogen, and the pharmaceutically acceptable salts thereof, also possess anti-tumor activity. Surprisingly, in addition, these novel fatty alkyl and alkenyl ether glycerophosphoethanolamines and salts have been discovered to also possess anti-psoriatic, anti-inflammatory, and anti-asthma activities.

SUMMARY OF THE INVENTION

The invention provides novel fatty alkyl and alkenyl ether glycerophosphoethanolamines bearing a defined heterocyclic (Het) substituent on the ethanolamine nitrogen and pharmaceutically acceptable salts of these compounds. The invention further provides a method of treating a tumor in a mammal with such compounds which comprises administering to the mammal an anti-tumor effective amount of said glycerophosphoethanolamines or pharmaceutically acceptable salts thereof. The invention further comprises a method of treating psoriasis which comprises administering to a mammal suffering therefrom anti-psoriatic effective amounts of said glycerophosphoethanolamines of the invention or pharmaceutically acceptable salts thereof. The invention further provides a method of treating inflammation which comprises administering to a mammal suffering therefrom an anti-inflammatory effective amount of said glycerophosphoethanolamines of the invention or pharmaceutically acceptable salts thereof. The invention further provides a method of treating a disease, such as asthma, associated with PAF which comprises administering to a mammal suffering therefrom a PAF-activity-inhibiting-effective amount of said glycerophosphoethanolamines of the invention or pharmaceutically acceptable salts thereof. The invention further provides a pharmaceutical composition comprising an anti-tumor, anti-psoriatic, anti-inflammatory, or anti-PAF-activity effective amount of said glycerophosphoethanolamines of the invention or pharmaceutically acceptable salts thereof together with a pharmaceutically acceptable carrier.

DETAILED DESCRIPTION OF THE INVENTION

Figure 1:
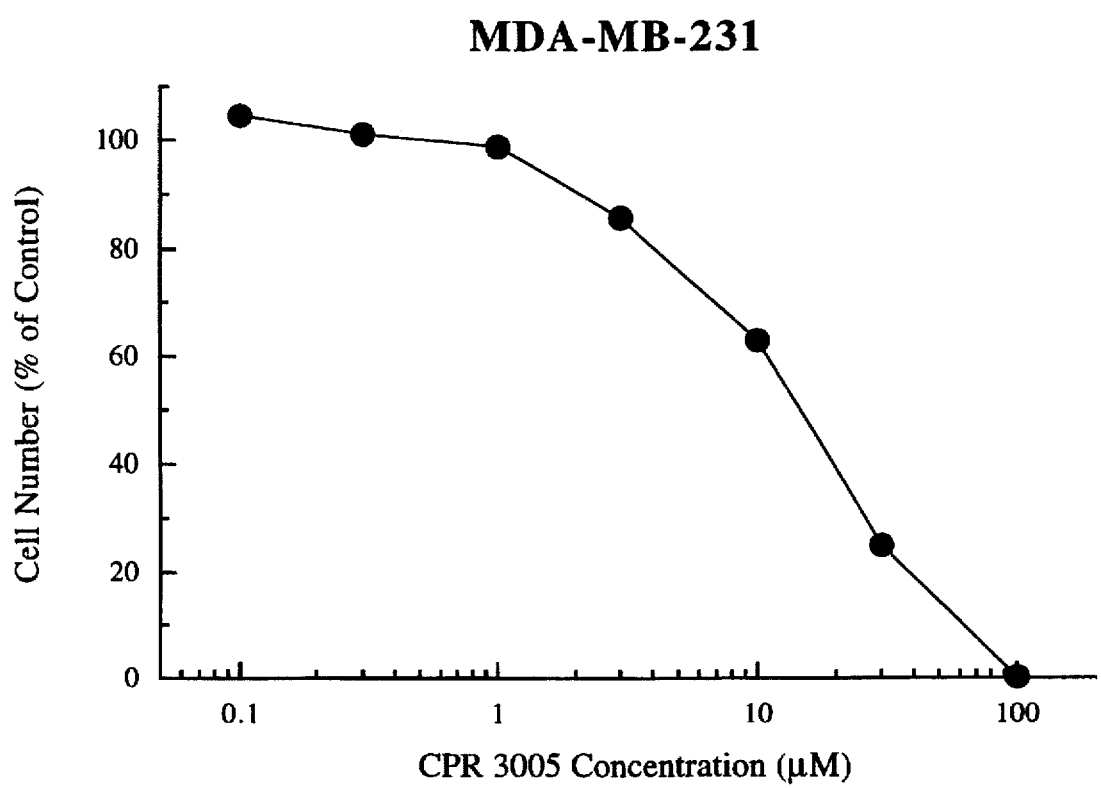
FIG. 1 is a graphical representation of results from an in vitro MDA-MB-231 cell inhibition assay of a compound of the invention, designated CPR 3005.

The present invention relates to novel fatty alkyl and alkenyl ether glycerophospholipids, also referred to as fatty alkyl and alkenyl ether glycerophosphoethanolamines, which bear a defined heterocyclic (Het) substituent on the ethanolamine nitrogen. The subject compounds are represented by the general formula (I):

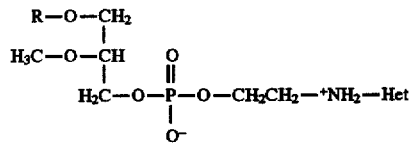

wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and Het represents a 5- to 9-membered monocyclic or bicyclic fused ring system with 1 to 3 hetero atoms, each hetero atom selected from the group consisting of oxygen, sulfur and nitrogen, and provided that Het is not an imidazolinyl ring system.

Imidazolinyl ring systems, which Het does not encompass, are disclosed in the commonly owned, co-pending U.S. patent application filed on the same day as this Application, having the title "N-SUBSTITUTED GLYCEROPHOSPHOETHANOLAMINES, and Attorney Docket No. 43549/199. This commonly owned, co-pending Application is incorporated herein by reference in its entirety.

The invention encompasses all optical and geometric isomers of the compounds of general formula (I) as well as salts the formula (I) compounds and of said isomeric forms thereof.

As used herein, R is selected from the group consisting of (1) substituted or unsubstituted, preferably unsubstituted, $C_{14-20}$ alkyl groups, preferably $C_{16-18}$ alkyl, such as, for example, tetra-, penta-, hexa-, hepta-, octa-, nonadecyl-, eicosyl-, or the branched analogs thereof; and (2) corresponding substituted or unsubstituted, preferably unsubstituted, $C_{14-20}$ alkenyl groups, preferably $C_{16-18}$ alkenyl, whereby a double bond of the alkenyl group does not involve the carbon atom of said alkenyl that is bonded to the oxygen of the glyceryl backbone. Both the aforementioned alkyl and alkenyl groups can be substituted at one or more carbons, preferably at one, with substituents which do not interfere with syntheses of the compounds during the synthetic steps of making them. Preferred substituents are halo, $C_{1-3}$ alkoxy or cyano. The term "halo" refers to any of the four halogens, chloro, bromo, iodo and fluoro, with chloro and fluoro being preferred.

Typical of the heterocyclic ring systems included within the term "Het" are such 5- to 9-membered rings, including single infused ring entities, such as, for example, among others, thiazolinyl, thiophenyl, thiazolyl, pyrilidinyl, 5,6-dihydro-4-H-oxazinyl, 5,6-dihydro-4-H-thiazinyl, pyrazinyl, benzothiazolyl and oxazolopyridinyl. The preferred ring is thiazolinyl. Preferably, it is the 2-carbon in the heterocyclic ring system which is bonded to the ethanolamine nitrogen. Said rings may also be substituted with one or more substituents, preferably one, such as $C^{1-3}$ alkyl, $C^{1-3}$ alkoxy or a polar substituent such as cyano, nitro, or methylsulfono.

I. CHEMISTRY

The compounds of the present invention may be prepared according to the following reaction scheme:

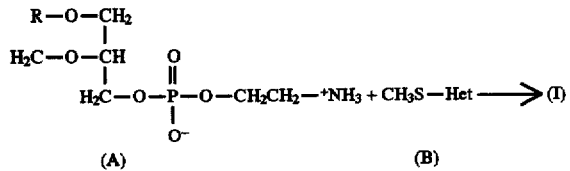

The reactants (A) and (B) are mixed in an appropriate organic solvent, e.g., isopropanol, and the mixture is refluxed for several hours. After cooling to room temperature, the solvent is evaporated off. Water is added and the pH is adjusted to about 4-4.5 by addition of acid, e.g., HCl solution. Conventional workup affords the desired end product (I).

The starting reactants of formula (A), 1-O-R-2-O-methyl-glycero-3-phosphoethanolamines, and their method of preparation are disclosed in the commonly owned, co-pending U.S. patent application filed on the same day as this application, having the title, "N-Substituted Glycerophosphoethanolamines", and having Attorney Docket. No. 43549/199. This commonly owned, co-pending application is incorporated herein by reference in its entirety.

The starting reactants (A) are identified as compounds (V) in said Application. The method of preparation of the starting reactants (A) is disclosed in said Application as follows:

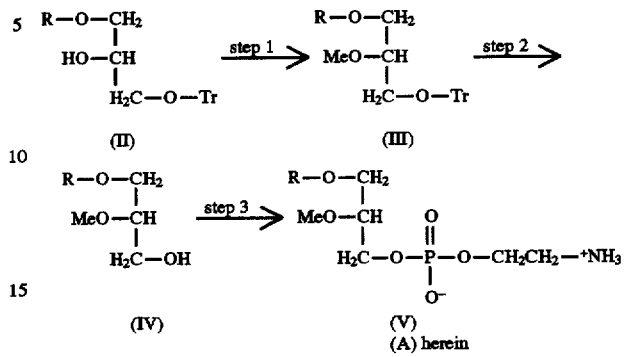

Step 1:
The compounds of Formula (II) are known in the literature or can be obtained by art-recognized procedures. See, for example, A. Hermetter and F. Paltauf, Procedures for the Synthesis of Ether Lipids, p. 393 et.seq., in H. K. Mangold and F. Paltauf, "Ether Lipids", Academic Press, 1983, and F. Paltauf and A. Hermetter, Methods Enzymol. Vol. 197, pp. 134-149 (1991). Also see Examples 1-3 which follow. Treatment of (II) under an inert atmosphere with potassium t-butylate and dimethylsulfate in an inert aprotic solvent such as toluene at elevated temperatures yields the corresponding 2-methoxy compound, 1-O-R-2-O-methyl-3-O-trityl-glycerol (III), also known as methyl-trityl-batylalcohol when R=n-octadecyl.

Step 2:
Removal of the trityl function in compound (III) to yield 1-O-R-2-O-methyl-glycerol (IV), also known as methyl-batylalcohol when R=n-octadecyl is readily accomplished by art-recognized procedures, e.g., by reacting a cooled solution (15°-18° C.) of Compound (III) in an inert aprotic solvent such as n-hexane with gaseous HCl.

Step 3:
The phosphoethanolamine moiety is introduced by reaction of the hydroxyl in Compound (IV) with $POCl_3$ and triethylamine at low temperatures (0°-4° C.) in an anhydrous solvent such as tetrahydrofuran, followed by reaction with ethanolamine, and treatment with aqueous dilute hydrochloric acid, to yield 1-O-R-2-O-methyl-glycero-3-phosphoethanolamine (V) (Compound A herein).

Working up the individual stepwise products indicated in the reaction scheme is advantageously carried out by standard methodologies, for example, by evaporating solvent from the reaction solution or precipitating the product from the reaction solution by dilution of the solution with an appropriate antisolvent (a solvent in which the product is less soluble than in the solvent of the reaction solution). The crude intermediate products obtained may be quite suitable, without further purification operations, for the preparation of the final products, which then may be purified. Particularly suitable methods for purifying the Formula I compounds are the conventional chromatographic methods, such as preparative thin-layer chromatography (TLC), column chromatography, adsorption chromatography, medium pressure liquid chromatography (MPLC) or high pressure liquid chromatography (HPLC).

The starting materials of Formula (B), methylthio-Het and their method of manufacture are described in the literature. Many of which are commercially available (for example, methylthiothiazoline (methylthio)thiophene, methylthiobenzothiazole, etc.) or can be prepared by reported procedure (e.g., for preparations of 2-methylthio-5-6-dihydro-4-H-oxazine and methylthio)oxazolopyridines. See R. C. Clapp, et al.; J. Heterocyclic Chem., pp. 107–108, 1968 and M. Y. Chu-Moyer, et al.; J. Org. Chem., Vol. 60, pp. 5721–5725, 1995, respectively.

The Formula I compounds have an asymmetric carbon atom (C2 position in the glyceryl backbone) in their structures. Consequently, these compounds may exist in the form of different R and S optically isomeric forms (enantiomers) or racemates. Substantially pure forms of either of the R- and S-isomer may be obtained, substantially free of the other, by the application of art-known resolution methodologies such as, for example, column chromatography using chiral columns, starting the preparation from the R- or S-isomer of an appropriate precursor, for example, the starting Compound (II) shown in the reaction scheme.

In addition, cis- and trans-geometric isomers may also be present in the subject compounds, e.g., when R in Formula I is $C_{14-20}$ alkenyl, due to the cis- and trans-configuration inherent with the double bond. Thus, by initially starting with an appropriate cis- or trans-precursor, the corresponding end product of the Formula I compound will be obtained.

A reference herein to the compounds of Formula (I) is to all optical/enantiomeric and all geometric isomers thereof, unless the reference is otherwise qualified.

Particular compounds within the scope of this invention, in racemic and enantiomeric form, are:

a. 1-O-n-octadecyl-2-methoxy-glycero-3-phospho-N-(2-thiazolinyl)-ethanolamine, also denoted as CPR 3005;
b. 1-O-n-hexadecyl-2-methoxy-glycero-3-phospho-N-(2-thiazolinyl)-ethanolamine;
c. 1-O-n-tetradecyl-2-methoxy-glycero-3-phospho-N-(2-thiophenyl)-ethanolamine;
d. 1-O-n-eicosyl-2-methoxy-glycero-3-phospho-N-(2-thiazolyl)-ethanolamine;
e. 1-O-(9-hexadecenyl)-2-methoxy-glycero-3-phospho-N-(2-pyrimidinyl)-ethanolamine;
f. 1-O-(2-chloro-n-octadecyl)-2-methoxy-glycero-3-phospho-N-[2-(5,6-dihydro-4-H-oxazinyl)]-ethanolamine;
g. 1-O-(2-cyano-n-hexadecyl)-2-methoxy-glycero-3-phospho-N-[2-(5,6-dihydro-4-H-thiazinyl)]-ethanolamine;
h. 1-O-(9-octadecenyl)-2-methoxy-glycero-3-phospho-N-(2-pyrazinyl)-ethanolamine;
i. 1-O-n-octadecyl-2-methoxy-glycero-3-phospho-N-(2-benzothiazolyl)-ethanolamine; and
j. 1-O-n-hexadecyl-2-methoxy-glycero-3-phospho-N-(2-oxazolopyridinyl)-ethanolamine.

All isomeric forms of the Formula I compounds, including pure enantiomeric and geometric isomers and mixtures thereof, are intended to be within the scope of this invention. Unless otherwise specified, the compounds of the following examples are in racemic form.

The invention also comprehends salts of the Formula I compounds. These salts include acid addition salts, such as, for example, those made with hydrochloric, hydrobromic, nitric, sulfuric, phosphoric, carbonic, acetic, citric or lactic acids. The salts may also include those made with bases, such as, for example, sodium hydroxide, potassium hydroxide or calcium hydroxide. The salts of the invention are made by conventional methods well known to those of ordinary skill in the art. The salts for therapeutic use of the Formula I compounds are pharmaceutically acceptable salts, as understood in the art.

II. UTILITY

The compounds of the subject invention and pharmaceutically acceptable salts thereof are useful chemopreventative and adjuvant agents in several aspects. They are useful for the treatment of cancerous tumors and also for treating inflammation, hyperproliferative skin diseases such as psoriasis, and asthma. The subject compounds and salts may be used alone for such indications or in combination with other compatible medicaments.

A. Anti-tumor Activity

The anti-tumor activity of both naturally occurring and synthetic glycerol-derived ether lipids has been reported in the literature, for example, see R. Andreesen, "Ether Lipids in the Therapy of Cancer", Prog. Biochem. Pharmacol., Vol. 22, pp. 118–131 (Karger, Basel 1988).

The testing procedures described In Example 13 below, using human tumor cell lines in in vitro assays, demonstrate the marked anti-tumor (or antineoplastic or oncolytic) activity of the subject compounds and pharmaceutically acceptable salts thereof, or illustrated by the compound CPR 3005.

Anti-tumor activity is to be expected against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testes, bladder, kidney and other urinary tissues, eye, brain and central nervous system, thryoid and other endocrine glands, leukemias (lymphocytic, granulacytic, monocytic), Hodgkin's disease, non-Hodgkin's lymphomas, multiple myeloma, etc. Herein the terms "tumor", "cancer" and "cancerous growths" are used synonymously.

The disclosed invention thus provides a method of treating a tumor in a mammal. The treatment comprises administering to said mammal an anti-tumor effective amount of a compound of Formula (I) or a pharmaceutically acceptable salt thereof. The invention also provides pharmaceutical compositions comprising an anti-tumor effective amount of a Formula (I) compound or a pharmaceutically acceptable salt thereof and a pharmaceutically acceptable carrier.

B. Anti-psoriasis Activity

Psoriasis is a chronic inflammatory dermatosis characterized, in part, by hyperproliferation of keratinocytes and release of pro-inflammatory cytokines. Compounds that reduce hyperproliferation of keratinocytes in vitro are therefore likely to have utility in the control of psoriasis. As will be shown, using the assay described in Example 14 below with the illustrative compound CPR 3005, the subject compounds and pharmaceutically acceptable salts thereof markedly inhibit proliferation of these cells in vitro, thus indicating that these compounds and salts are useful in ameliorating psoriasis.

The instant invention thus provides a method of treating psoriasis in a mammal afflicted with same comprising administering to said mammal an effective anti-psoriatic amount of a compound of Formula I or a pharmaceutically acceptable salt thereof. It also provides pharmaceutical compositions comprising an effective anti-psoriatic amount of a compound of Formula I or a pharmaceutically acceptable salt thereof and a pharmaceutically acceptable carrier.

C. Anti-inflammatory Activity

Inflammation is a complex process, involving a variety of cell types including macrophages. See, for example, S. L. Kunkel, "Inflammatory Cytokines", pp. 1–15, in Manual of Vascular Mediators, P. A. Ward, Editor, produced by the publishers of Hospital Practice. References relative to macrophages are numerous, including, for example, J. Immunology, Vol. 119, pp. 950–954 (1977) and Cell, Vol. 15, pp. 261–267 (1978).

Macrophages are activated by infection and by a wide variety of non-infectious irritants and proinflammatory agents. Upon activation, macrophages participate in a variety of reactions. They may phagocytize bacteria and kill them by either oxygen-dependent or oxygen-independent pathways. With respect to the oxygen-dependent pathways, activation of macrophages induces them to increase oxygen consumption and produce reactive oxygen species (for example, radicals such as superoxide). Production of reactive oxygen species by activated macrophages is associated with inflammatory responses. In addition, on activation, macrophages release a variety of inflammatory cytokines, including several interleukins and tumor necrosis factor α (TNFα). Inhibition of any of these activation-related processes can lead to reduced inflammation.

For these reasons, macrophage activation is of critical importance in studies of the inflammatory process. Agents that reduce macrophage activation are likely to have utility as anti-inflammatories.

As will be shown, using the assay described in Example 15 below with the illustrative compound CPR 3005, the subject compounds and pharmaceutically acceptable salts thereof markedly reduce macrophage activation, thus indicating that these compounds and salts are useful in ameliorating inflammation.

The subject compounds are thus useful in the treatment of acute and chronic inflammatory diseases, such as, for example, dermatitis, conjunctivitis, bursitis, rheumatoid arthritis and the like.

The instant invention thus provides a method of treating inflammation in a mammal afflicted with same comprising administering to said mammal an effective anti-inflammatory amount of a compound of Formula (I) or a pharmaceutically acceptable salt thereof. It also provides pharmaceutical compositions comprising an effective anti-inflammatory amount of a compound of Formula I or a pharmaceutically acceptable salt thereof and a pharmaceutically acceptable carrier.

D. PAF Antagonism

Platelet-activating factor (PAF) 1-O-$C_{16-18}$alkyl-2(R)-acetyl-sn-glyceryl-3-phosphocholine), its effect on platelets and its biological effects have been the subject of many reported studies since its discovery in the early 1970s. Typical PAF literature reviews include those of Dean A. Handley, Pharmacological Methods in the Controlled Information, pp. 23–58, 1989, and Matyas Koltai, et al., Drugs, Vol. 42, pp. 9–29, 1991.

Platelet Activating Factor (PAF) has been shown to be a mediator of inflammation and has been found in lung fluids of asthma patients. PAF is a chemoattractant and encourages the migration of neutrophiles and eosinophiles to sites of inflammation and to the airways of asthmatic patients. Moreover, PAF has been shown to be a powerful bronchial constrictor of the airways of asthmatic patients. In addition, PAF has been found in the psoriatic lesions of psoriasis patients. Accordingly, antagonists of PAF have potential utility in treating inflammatory diseases, including rheumatoid arthritis, asthma, psoriasis and immediate and delayed type hypersensitivity reactions.

The understanding of PAF has been markedly advanced by the development and availability of PAF antagonists and their clinical implications. As noted in Handley, page 43, supra, there are intense and focused studies on PAF, and a prominent pharmaceutical effort to develop antagonists, and clinical trials of PAF antagonists in humans are in progress.

It has now been found that the subject compounds possess marked PAF antagonist activity. Example 16 hereafter demonstrates the inhibition of the constrictor activity of PAF on the test animal airway, as illustrated with the compound CPR 3005. The subject compounds are thus useful in ameliorating PAF related disease states, including PAF-induced bronchial asthma.

The subject invention thus provides a method of inhibiting PAF activity in a host mammal having a susceptible PAF-induced pathophysiological condition which comprises the administration to said mammal of an effective PAF antagonist amount of Formula (I) compound or a pharmaceutically acceptable salt thereof. The invention also provides pharmaceutical compositions comprising an effective PAF antagonist amount of a Formula (I) compound or a pharmaceutically acceptable salt thereof and a pharmaceutically acceptable carrier. For conditions such as PAF-induced bronchial asthma, pharmaceutical compositions for inhalation administration are suitable, such as aerosol inhalation spray, for example, in a metered dose device.

Among the mammals that may be treated with the subject compounds, salts, therapeutic methods and formulations of the invention are, of course, humans.

III. FORMULATIONS

Formulations of the present invention, for medical use, comprise an active compound, i.e., a Formula (I) compound or a pharmaceutically acceptable salt thereof, together with an acceptable carrier for it and optionally other therapeutically active ingredients. The carrier must be pharmaceutically acceptable in the sense of being compatible with the other ingredients of the formulation and not deleterious to the recipient of it.

The formulations include those suitable for oral, rectal, parenteral (including subcutaneous, intradermal, intramuscular and intravenous), nasal, or bronchial administration. Preferred formulations are those suitable for oral or parenteral administration. Topical formulations are also included, for example, anti-psoriatic usage.

It is noted that the Formula (I) compounds typically decompose on heating above about 200° C. This characteristic may need to be taken into consideration in, for example, preparing tablets on a commercial scale where the heat of compression may be a factor. The Formula (I) compounds are also rather insoluble in water and, accordingly, liquid formulations which account for this factor may be made according to art-recognized pharmaceutical techniques. Examples of these techniques include an injection wherein the active compound is dissolved in a suitable solvent or co-solvent such as an appropriate polyethylene glycol, or a propylene glycol or the like; a sealed gelatin capsule enclosing an oily solution of the active compound; a suppository of the active compound in a conventional suppository base such as cocoa butter; or a liposome formulation, for example, the active compound and a glycerophospholipid such as phosphatidylcholine. In any event, the aforementioned characteristics of the Formula (I) compounds are not uncommon in the pharmaceutical area and, accordingly, art-recognized pharmaceutical techniques are employed to prepare appropriate formulations for such compounds as those of Formula (I) or pharmaceutically acceptable salts thereof.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as suspension, solution, syrup, elixir, emulsion, dispersion, liposome preparation, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulations suitable for parenteral administration conveniently comprise a sterile preparation of the active compound in, for example, a polyethylene glycol 200 or propylene glycol solution which is preferably isotonic with the blood of the recipient.

Useful formulations also comprise concentrated solutions or solids containing the compound of Formula (I) which upon dilution with an appropriate solvent give a solution suitable for parenteral administration.

Compositions suitable for inhalation administration, for example, for treating bronchial asthma, wherein the carrier is a solid include a micronized powder or liquid formulation having a particle size in the range of from about 5 microns or less to about 500 microns, for rapid inhalation through the oral passage from a conventional inhalation squeeze or spray container. Suitable liquid nasal compositions include conventional nasal sprays, nasal drops and the like, of aqueous solutions of the active ingredient and optional adjuvants.

Preparations for topical or local applications, which are, for example, conventional for anti-psoriatic usage, and may be useful in treatment of certain cancers, comprise aerosol sprays, lotions, gels, ointments, transferosomes, plasters, etc. and pharmaceutically acceptable vehicles therefore such as, for example, lower aliphatic alcohols, polyols such as glycerol, polyethyleneglycerol, esters of fatty acids, oils and fats, silicones, and other conventional topical carriers, for example, liposomes.

In topical formulations, the compounds of Formula (I) are preferably utilized at concentrations of from about 0.1% to about 5.0% percent by weight.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

The compounds of Formula (I) and salts thereof of the invention are to be administered under the guidance of a physician or veterinarian.

The amount of compound of Formula (I) or salt thereof required to be effective for each of the herein indicated activities will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound or salt to be administered. In general, the pharmaceutical compositions of this invention contain from about 0.5 to about 500 mg, and preferably, from about 5 mg to about 350 mg of the active ingredient, preferably in a unit dosage form, for each of the indicated activities.

A suitable effective dose is in the range of about 0.1 to about 200 mg/kg body weight per day, preferably in the range of about 1 to about 100 mg/kg per day, calculated as the non-salt form of compound of Formula (I). The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 7.5 to about 1500 mg per day, and a typical dose would be about 800 mg per day. If discrete multiple doses are indicated, treatment might typically be 200 mg of a compound of Formula (I) given 4 times per day.

In general, the pharmaceutical compositions of this invention contain from about 0.5 mg to about 500 mg and, preferably, from about 5 mg to about 350 mg of active ingredient (compound of Formula (I) per se or as part of a pharmaceutically acceptable salt), preferably in a unit dosage form, for each of the indicated activities of the invention.

The following examples are intended to illustrate and not to limit the scope of the present invention.

EXAMPLE 1

A. Octadecylmethanesulfonate

500 Grams (1.85 mol) of 1-octadecanol is suspended with stirring in 2500 ml methylene chloride and 224.5 g (2.22 mol; 310 ml) triethylamine is added with cooling (cold water). 254 Grams (2.215 mol; 171.5 ml) of methanesulfochloride dissolved in 500 ml methylene chloride is then added in such a way that the reaction temperature is maintained between 20° and 25° C. Stirring at ambient temperature (18°–23° C.) is continued for 1.5 hours. The methylene chloride is removed under vacuum at a temperature of 35° C. maximum. To the remaining syrup, 1000 ml of ethanol/water (1/1; v/v) are added and remaining methylene chloride is completely removed under vacuum. An additional 2500 ml ethanol/water (1/1; v/v) is added with stirring. The resulting crystallizate is filtered off, washed three times with ethanol/water (1/1; v/v) and air-dried to yield 641 g (99.4%) of octadecylmethanesulfonate; m.p. 60°–61° C.; water content does not exceed 0.5%.

B. By utilizing an equivalent amount of an appropriate $C_{14-20}$ alkanol or alkenol in the foregoing procedure, the following methanesulfonates are obtained:

n-tetradecylmethanesulfonate;
n-hexadecylmethanesulfonate;
n-eicosylmethanesulfonate;
cis-9-octadecenylmethanesulfonate;
trans-9-octadecenylmethanesulfonate;
cis-9-hexadecenylmethanesulfonate;
trans-9-hexadecenylmethanesulfonate;
2-chloro-n-octadecylmethanesulfonate;
2-methoxy-n-octadecylmethanesulfonate; and
2-cyano-n-hexadecylmethanesulfonate.

EXAMPLE 2

A. 1-O-n-Octadecyl-Glycerol (Batylalcohol)

In an argon atmosphere, 79.2 g (1.2 mol) powdered potassium hydroxide (purity 85%) is suspended in 1680 ml dimethylsulfoxide. 118.88 Grams (0.9 mol) solketal (rac-1, 2-isopropylidene-glycerol) is added and the mixture is stirred for one hour at ambient temperature (18°–23° C.). Stirring is continued and 209.16 g (0.6 mol) octadecyl-methanesulfonate is added. Stirring is continued for another three hours and the reaction mixture is kept overnight at ambient temperature.

No argon atmosphere is necessary. A mixture of 840 ml methanol and 336 ml conc. HCl is added and the reaction mixture is refluxed with stirring for one hour. Stirring is continued for another two hours, followed by cooling the reaction mixture to 30° C. Then 1040 ml methanol is added and stirring is continued for 10 minutes. Upon keeping the reaction mixture at 4° C. overnight, a precipitate is formed which is filtered off and washed with 300 ml methanol/water (1:1; v/v) and 1000 ml water. The crude product is then suspended (without drying) in 6400 ml water and the suspension is vigorously stirred for 30 minutes. The precipitate is filtered off and washed with three portions of 500 ml water. The crystallizate is dried under vacuum over phosphorous pentoxide to yield 190 g (92%) of batylalcohol; m.p. 68°–70° C.

B. 
By substituting an equivalent amount of each methanesulfonate of Example 1-B for the octadecyl-methanesulfonate of Example 2-A, each corresponding 1-O-R-glycerol is obtained.

EXAMPLE 3

A. 1-O-n-Octadecyl-3-O-Trityl-Glycerol (Trityl-batylalcohol) (II)

51.69 Grams (150 mmol) of batylalcohol and 62.73 g (225 mmol) freshly recrystallized tritylchloride are dissolved at 35° C. in 350 ml methylene chloride. (Note: It is recommended that the tritylchloride be freshly recrystallized from halpasol, tradename for a petroleum ether fraction, b.p. 100°–120° C.). During 15 minutes, 22.77 g (225 mmol; 31.38 ml) triethylamine is added dropwise to the stirred solution at 30°–35° C. (cooling with a water bath). The reaction is continued for six hours at ambient temperature. (Note: It is recommended that a control TLC be done to make sure that the reaction is complete). The solution is then washed with 300 ml of a NaHCO$_3$ solution (1%), dried over anhydrous sodium sulfate, filtered and evaporated under vacuum. The oily residue (155 g) is dissolved in 660 ml acetonitrile by warming up to 70° C. with stirring. After cooling to room temperature the title product crystallizes (preferentially after adding a few seed crystals). Crystallization is completed by standing overnight at ambient temperature. The crystallizate is filtered off to yield 82.5 g (93.7%) of crude product (m.p. 53°–55° C.) which can be used for the following step without purification. Recrystallization from halpasol (310 ml) yields 71 g (80%) of pure tritylbatylalcohol.

B. 
In a similar way, introduction of the 3-O-trityl function is accomplished for each 1-O-R-glycerol of Example 2-B.

EXAMPLE 4

1-O-n-Octadecyl-2-O-Methyl-3-O-Trityl-Glycerol (Methyl-Trityl-Batylalcohol) (III)

Under an inert atmosphere (argon or nitrogen), 586.0 g (1 mol) trityl-batylalcohol (III) and 112.2 g (1 mol) potassium-t-butylate are dissolved in 2000 ml toluene with stirring, heated to 85° C. and within 30 minutes 63.07 g (0.5 mol) dimethylsulfate (47.4 ml) are added. The temperature is raised to 100° C. and then the reaction mixture is refluxed for one hour. After cooling to 98° C., 112.1 g (1 mol) potassium-t-butylate and 63.07 g (0.5 mol) dimethylsulfate are added within 30 minutes while the mixture is refluxed. Refluxing with stirring is continued for 6 hours; then the mixture is kept overnight at room temperature. The mixture is extracted with water (3×2000 ml) and the organic layer is evaporated under vacuum to yield 620 g of the 1-O-n-octadecyl-2-O-methyl-3-O-trityl-glycerol (methyl-tritylbatylalcohol) as an oily residue, which can be used in the following detritylation step without purification.

TLC:KG 60 F (Merck);

Mobile Phase: CH$_2$Cl$_2$; Rf: 0.20; Rf of an impurity (<5%) 0.02; visualized by iodine; (more sensitive visualization is achieved with chromate-sulphuric acid).

Pure methyl-trityl-batylalcohol (III) can be obtained by MPLC:

Apparatus: Waters PREP 500;

2 Silica cartridges (equals approx. 800 g silica, normal phase);

Mobile Phase: CH$_2$Cl$_2$;

Sample: 15 g raw (III) dissolved in 30 ml CH$_2$Cl$_2$;

Axial Pressure: 38 bar;

Internal Pressure: 9–15 bar;

Flow Rate: 200 ml/min;

Detection: RI-detector; Split 1:100

EXAMPLE 5

1-O-n-Octadecyl-2-O-Methyl-Glycerol (Methyl-Batylalcohol) (IV)

616.3 grams (calculated with impurities, 1 mol=600.9 g) of crude methyl-trityl-batylalcohol (III) from Example 4 is dissolved in 1350 ml n-hexane and cooled to 15°–18° C. Within two hours 44 g (1.21 mol) gaseous HCl is passed into the stirred solution at the same temperature. After 30 minutes, tritylchloride starts to precipitate. The mixture is stirred for an additional hour at 15°–18° C. The precipitate is filtered off and washed with 250 ml cooled (16° C.) n-hexane. After air-drying, 214 g (76.76%) tritylchloride are obtained. The hexane phases are combined and kept at −20° C. overnight. The crystallized product is filtered off and washed with 220 ml cold (−20° C.) n-hexane. After air-drying, 331.35 g (92.4%) crude methyl-batylalcohol (IV) are obtained. (Note: Depending on the amount of co-crystallizing trityl derivatives, the yield may exceed 100%. Another impurity is n-octadecanol which should be removed in any case because in the next reaction step it may form phospholipids that cannot be separated from the product.)

Purification: 500 Grams raw methyl-batylalcohol are dissolved in 1500 ml toluene and slowly filtered through a bed of 1500 g alumina on a glass frit. (Note: The alumina bed is prepared by filtering a slurry of alumina in toluene). The alumina is washed with 1500 ml toluene. The toluene phases are combined and evaporated to dryness under reduced pressure. Recrystallization from n-hexane at −20° C. yields 402.2 g methyl-batylalcohol (IV) of sufficient purity to be used in the next step.

TLC:KG 60F (Merck);

Mobile Phase: CH$_2$Cl$_2$/EtOAc (4/1, v/v);

Rf: 0.40;

Visualized by iodine or by chromate-sulphuric acid.
Purification of raw methyl-batylalcohol by MPLC:
  Steel column: 50×500 mm, Amicon (Grace);
  Matrex silica: 20–45μ, normal phase (Grace);
  Mobile phase: $CH_2Cl_2$/EtOAc (22/3; v/v);
  Sample: 20.7 g raw (IV) dissolved in 25 ml $CH_2Cl_2$;
  Internal pressure: 8–12 bar;
  Flow rate: 156 ml/min;
  Detection: RI-detector or TLC;
  Pure methyl-batylalcohol (IV): m.p. 43°–44° C.

EXAMPLE 6

1-O-n-Octadecyl-2-O-Methyl-Glycero-3-Phosphoethanolamine (V)

A mixture of 40 ml anhydrous tetrahydrofuran (THF) and 36.8 g $POCl_3$ (240 mmol) is cooled to 0° C. Into this stirred solution, a mixture of 72 g (200 mmol) methyl-batylalcohol (IV), 36.4 g (360 mmol) triethylamine and 240 ml THF is added dropwise as the temperature is maintained at 0°–4° C. Some material precipitates. The cooling device is removed and a mixture of 14.7 g (240 mmol) ethanolamine, 36.4 g (360 mmol) triethylamine and 180 ml THF is added to the stirred solution within 15 minutes. The temperature rises to about 55° C. and stirring is continued at this temperature for one hour. After cooling to 15° C., a mixture of 30 ml conc. HCl and 170 ml water is added at 25°–30° C. The reaction mixture is allowed to come to ambient temperature and stirring is continued for one hour. The water layer is removed and the THF layer is diluted with 600 ml methylenechloride. 50 grams of sodium bicarbonate are added with vigorous stirring. After continuing stirring for 15 minutes, anhydrous sodium sulfate is added and stirring is continued for a few minutes. The inorganic material is removed by filtration and the solvent is evaporated under reduced pressure. The honey-like residue is taken up in 500 ml methylene chloride and a slight turbidity is removed by adding charcoal followed by filtration over a glass filter. Half of the methylenechloride is distilled off and 200 ml acetone are added. Upon cooling to 0° C. for two hours, 91.2 g (94.7%) of raw product (V) precipitates. This material is dissolved in 800–900 ml boiling isopropanol. The solution is passed over a filter and cooled to room temperature. On standing overnight at room temperature 86.3 g (89.5%) of crystalline 1-O-n-octadecyl-2-O-methyl-glycero-3-phosphoethanolamine (V) is obtained.

TLC:KG 60 F (Merck);
  Mobile phase 1: $CHCl_3$/$CH_3OH$/c. $NH_3$; 65/35/5 per vol.;
  Rf: 0.22;
  Mobile phase 2: $CHCl_3$/$CH_3OH$/acOH/HOH; 100/60/20/5 per vol.;
  Rf: 0.18;
  Visualized by chromate-sulphuric acid.
Purification of (V) by MPLC:
  Steel column: 50×500 mm, Amicon (Grace);
  Matrex silica: 20–45μ, normal phase (Grace);
  Sample: 30 g (V) dissolved in 100 ml $CH_2Cl_2$ and 20 ml $CH_3OH$;
  Internal pressure: 8–10 bar;
  Flow rate: 78–156 ml/min;
  Detection: RI-detector or TLC.

EXAMPLE 7

By following the procedures outlined in Examples 4–6, except that an equivalent amount of each 1-O-R-3-O-trityl-glycerol of Example 3-B is employed as the starting material, the following respective compounds of Formula (A) are obtained: the corresponding 1-O-n-tetradecyl-, 1-O-n-hexadecyl-, 1-O-n-eicosyl-, 1-O-(9-octadecenyl)-, 1-O-(9-hexadecenyl)-, 1-O-(2-chloro-n-octadecyl)-, 1-O-(2-methoxy-n-octadecyl)-, and 1-O-(2-cyano-n-hexadecyl)-derivatives of 2-O-methyl-glycero-3-phosphoethanolamine.

EXAMPLE 8

1-n-O-Octadecyl-2-O-Methyl-Glycero-3-Phospho-N-(2-Thiazolinyl)-Ethanolamine-(CPR 3005)

A mixture of 1-O-n-octadecyl-2-O-methyl-glycero-3-phosphoethanolamine (2.0 g, 4.15 mmol), 2-methylthiothiazoline (0.8 g, 6.0 mmol) and isopropyl alcohol (25 ml) are refluxed overnight (about 12 hours) under nitrogen. The resultant reaction mixture is cooled to room temperature (20°–25° C.) and concentrated under reduced pressure. Water (25 ml) is added to the residue and the pH of the suspension is brought to 4.0–4.5 by dropwise addition of 4N HCl, followed by extraction with a 2:1 mixture v/v of chloroform and methanol (2×100 ml). The organic layer is separated, dried over sodium sulfate, and filtered. The filtrate is concentrated under reduced pressure and the resultant residue stirred with 25 ml ether overnight. The thus-obtained white solid material is separated by filtration to afford the 1-n-O-Octadecyl-2-O-Methyl-Glycero-3-Phospho-N-(2-Thiazolinyl)-Ethanolamine-(CPR 3005) product. Purification by column chromatography (silica gel, 230–400 mesh, 20×5 cm, as stationary phase and $CHCl_3$/MeOH/$NH_4OH$(30%), 65/35/5, v/v/v, as mobile phase) affords about 0.52 g of 1-O-n-octadecyl-2-O-methyl-glycero-3-phospho-N-(2-thiazolinyl)-ethanolamine.

Thin layer chromatography (TLC) [4×8 cm silica gel (0.25 mm thickness) plate and $CHCl_3$/MeOH/$NH_4OH$ (30%), 65/35/5, v/v/v, as eluent] gives a single spot, Rf value 0.58. Liquid secondary ion mass spectrometry (LSIMS)(+ve ion mode, 3-nitrobenzylalcohol matrix): $(M+H)^+$ at m/e 567.3 for $C_{27}H_{56}N_2O_6P_1S_1$. $^1H$, $^{31}P$ and $^{13}C$ NMR analyses are consistent with the structure.

EXAMPLE 9

The procedure of Example 8 is followed, except that an equivalent amount of each 1-O-R-2-O-methyl-glycero-3-phospho-ethanolamine of Formula (A) of Example 7 is employed as the starting material, to yield the following respective compounds of Formula (I): the corresponding 1-O-n-tetradecyl-, 1-O-n-hexadecyl-, 1-O-n-eicosyl-, 1-O-(9-octadecenyl)-, 1-O-(9-hexadecenyl)-, 1-O-(2-chloro-n-octadecyl)-, 1-O-(2-methoxy-n-octadecyl)- and 1-O-(2-cyano-n-hexadecyl)-derivatives of 2-O-methyl-glycero-3-phospho-N-(2-thiazolinyl)-ethanolamine.

EXAMPLE 10

Additional compounds of Formula (I) prepared by the procedure of Example 8 with an equivalent amount of the appropriate reactants (A) and (B) are:
  1-O-n-hexadecyl-2-O-methyl-glycero-3-phospho-N-(2-thiophenyl)-ethanolamine;
  1-O-n-tetradecyl-2-O-methyl-glycero-3-phospho-N-(2-pyrazinyl)-ethanolamine;
  1-O-n-eicosyl-2-O-methyl-glycero-3-phospho-N-(2-benzothiazolyl)-ethanolamine; and
  1-O-n-hexadecyl-2-O-methyl-glycero-3-phospho-N-(2-pyrimidinyl)-ethanolamine.

EXAMPLE 11

1-O-n-Hexadecyl-2-O-Methyl-Glycero-3-Phospho-N-(2-Thiazolinyl)-Ethanolamine

The Procedure of Example 8 is followed except that an equivalent amount of 1-O-hexadecyl-2-O-methyl-glycero- 3-phosphoethanolamine is used as the starting material (A) to yield the titled compound as the final product.

EXAMPLE 12

By following the procedure of Example 8, except that an equivalent amount of the appropriate methylthio-Het reactant (B) is substituted for the 2-methylthiothiazoline used therein, there are obtained as respective products the following: the Formula (I) compounds wherein R is 0-n-octadecyl and Het is 2-thiophenyl, 2-thiazolyl, 2-pyrimidinyl, 2-(5,6-dihydro-4-H-oxazinyl), 2-(5,6-dihydro-4-H-thiazinyl), 2-pyrazinyl, 2-benzothiazolyl and 2-oxazolopyridinyl.

EXAMPLE 13

Assay for Anti-Tumor/Antineoplastic Activity

Figure 2:
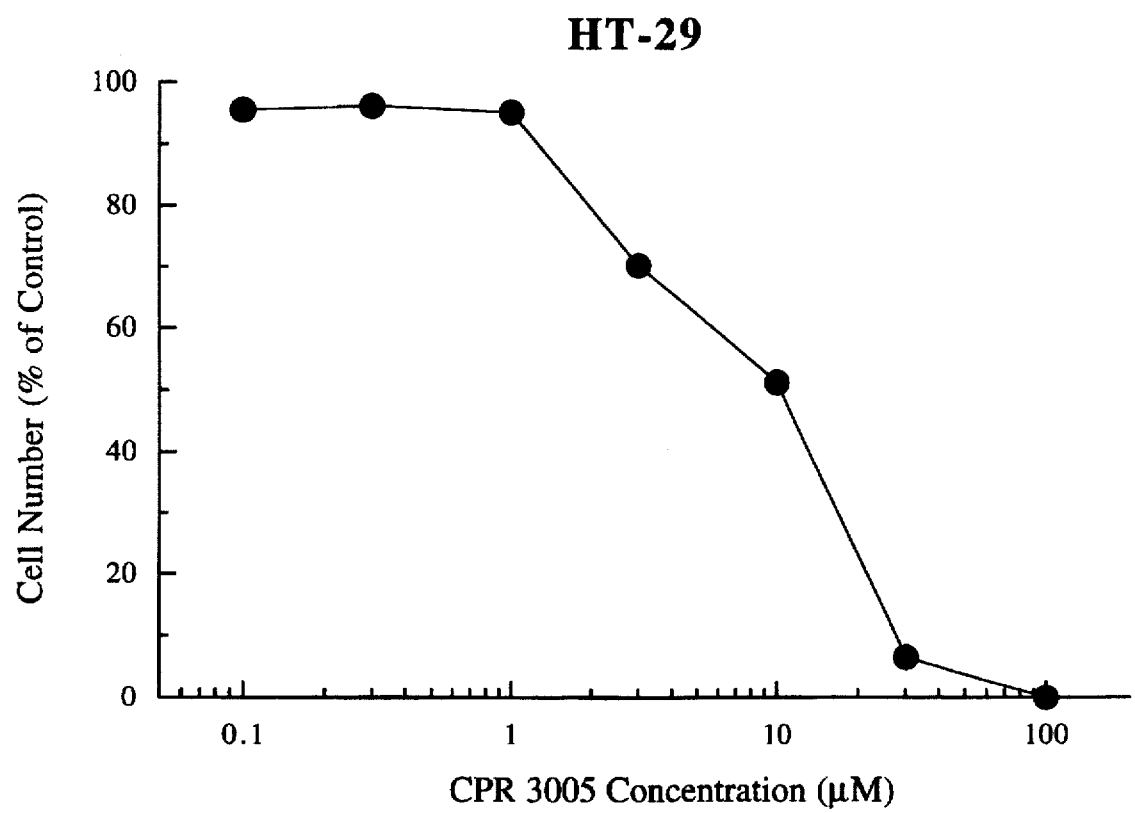
FIG. 2 is a graphical representation of results from an in vitro HT 29 cell inhibition assay of a compound of the invention, designated CPR 3005.

1. Human tumor cell lines, available from the American Type Culture Collection (ATCC):
   a. MDA-MB-231 (ATCC HTB 26): an estrogen receptor negative human breast carcinoma cell line (attachment dependent); and
   b. HT-29 (ATCC HTB 38): a human colon carcinoma cell line (attachment dependent).
2. Culture media:
   a. for cell line 1-a: Dulbecco's Modified Eagle's Medium (DMEM) plus 10% Fetal Bovine Serum (FBS); and
   b. for cell line 1-b: 1:1 DMEM and Ham's F-12 (DMEM/F12) plus 10% FBS.
3. Standard protocol for culturing cell lines: in T-75 or T-150 flasks; 37° C.; 95% air; 5% $CO_2$; 100% humidity.
   a. Cell lines 1-a and 1-b are passaged when approximately 80% confluent; with trypsin (1 mg/ml) and EDTA (1 mM EDTA in Ca-Mg free Hank's balanced salt solution); at a 1:4 to 1:5 split.
   b. All procedures are performed aseptically in a Class II biological safety cabinet using standard BL-2 containment procedures. At approximately monthly intervals, fresh cells are thawed from liquid nitrogen storage in order to prevent genetic drift in stock cell lines.
4. Assay Procedure:
   a. After cell passage, count cells with a hemocytometer;
   b. Adjust concentration to approximately 5,000 cells per 100 µL;
   c. Pipette 100 µL cell suspension per well of a standard 96-well microtiter plate;
   d. Preincubate 24 hours to allow cells to attach;
   e. Add 100 µL of test compound dispersed in phosphate buffered saline (PBS) and diluted in DMEM (for MDA-MB-231 cells) or DMEM/F12 (for HT-29 cells) to achieve final concentration levels ranging from 0 to 100 µM; and
   f. Incubate 48 hours under standard culture conditions and determine end points.
5. End Point:
   a. Remove media and add 100 µL/well of cold (4° C.) 10% (w/v) trichloroacetic acid (TCA) in water;
   b. After 1 hour at 4° C., remove TCA and rinse cells 5 times with tap water;
   c. Air-dry plates;
   d. Add 50 µL/well of 0.4% (w/v) sulforhodamine B (SRB) in 1% (v/v) acetic acid in water;
   e. After 30 minutes at room temperature, rinse cells 4 times with 1% (v/v) acetic acid in water to remove residual stain;
   f. Air-dry plates;
   g. Dissolve stain by adding 100 µL/well of unbuffered Tris base, pH 10.5;
   h. Read absorbance at 564 nm using a standard 96-well microtiter plate reader. Absorbance readings are linear with dye concentrations below 1.8 absorbance units. To reduce absorbance, decrease wavelength at which measurements are taken.
6. Data Analysis:
   a. For a single point reading, a higher absorbance indicates a higher cell number;
   b. Control—no test compound present in culture medium;
   c. Background—no cell and no test compound present in culture medium;
   d. Calculate CN (cell number as % of Control):

$$CN = \frac{A(\text{test compound}) - A(\text{background})}{A(\text{control}) - A(\text{background})} \times 100$$

where A(test compound) is absorbance with test compound present in the culture medium, A(control) is absorbance of control, and A(background) is absorbance of background;

7. Results are represented in FIGS. 1 and 2, which illustrate the marked inhibition of cell growth at concentrations above 3 µM by the compound tested (CPR 3005).

EXAMPLE 14

Assay for Anti-psoriatic Activity by Inhibition of Keratinocyte Proliferation 1. Cell line: PAM-212 murine keratinocyte cell line isolated and cultivated from newborn BALB/c mice (see S. H. Yuspa et al., Cancer Research, Vol. 40, pp. 4694–4703, 1980) that appears to retain many characteristics of normal keratinocytes.

2. Culture medium: 1:1 DMEM and Ham's F-12 with 10% FBS.

3. Culture conditions are the same as those described previously in parts 3(a) and 3(b) of Example 13.

4. Methodology is the same as that described previously in part 4 of Example 13, except that, with reference to part 4(b), cell concentration is adjusted to 1,000 cells per 100 µL (rather than 5,000 cells per 100 µL), and, with reference to part 4(e), test compounds are diluted in DMEM/F12 prior to addition to cell wells.

5. End point determination and data analysis are done as described previously in parts 5 and 6 of Example 13.

Figure 3:
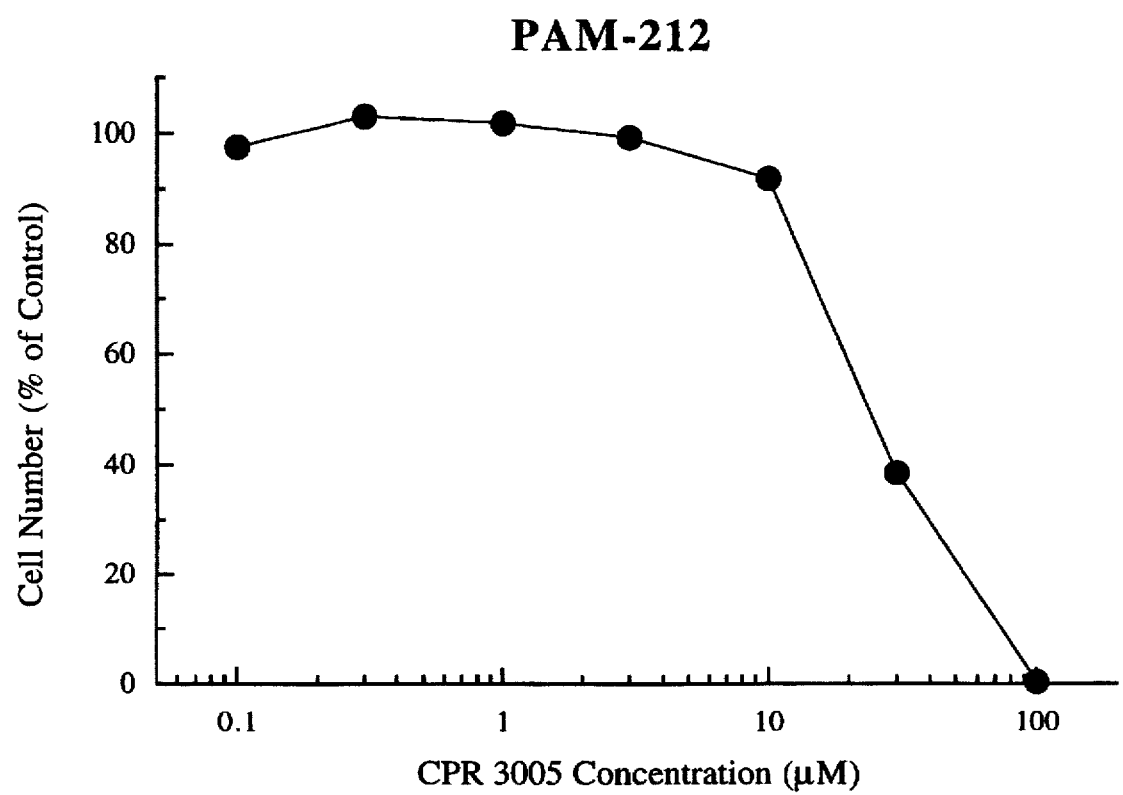
FIG. 3 is a graphical representation of results from an in vitro PAM-212 cell inhibition assay of a compound of the invention, designated CPR 3005.

6. The results are presented in FIG. 3, which illustrates the marked inhibition of keratinocyte-proliferation, and consequently the marked anti-psoriatic activity, at concentrations above 10 µM of the compound tested (CPR 3005).

EXAMPLE 15

Assay for Anti-inflammatory Activity by Inhibition of Macrophage Chemiluminescence The RAW 264.7 cell line (available from the ATCC under accession no. TIB 71) is a murine monocyte/macrophage line the cells of which show many of the differentiative functions of a macrophage. Like macrophages, the cells are capable of phagocytosis and undergo a respiratory burst (increased oxygen consumption) and production of oxygen radicals (e.g., superoxide) in response to appropriate activation signals. Agents that inhibit the activation of these cells in vitro, so as to inhibit the respiratory burst and corresponding production of oxygen radicals associated with the activation, are therefore inhibitors of macrophage activation and critical steps in inflammatory processes. These agents are then likely to be anti-inflammatories.

The respiratory burst and corresponding production of oxygen radicals that accompany macrophage activation can be measured in a variety of ways, including chemiluminescence based on the reaction of the oxygen radicals with luminol added to the culture medium (see M. A. Trush et al., Methods in Enzymology, Vol. 57, pp. 462–494). Indeed, chemiluminescence generated from luminol in the culture medium of macrophage cell lines is recognized in the art as a marker of macrophage activation.

Figure 4:
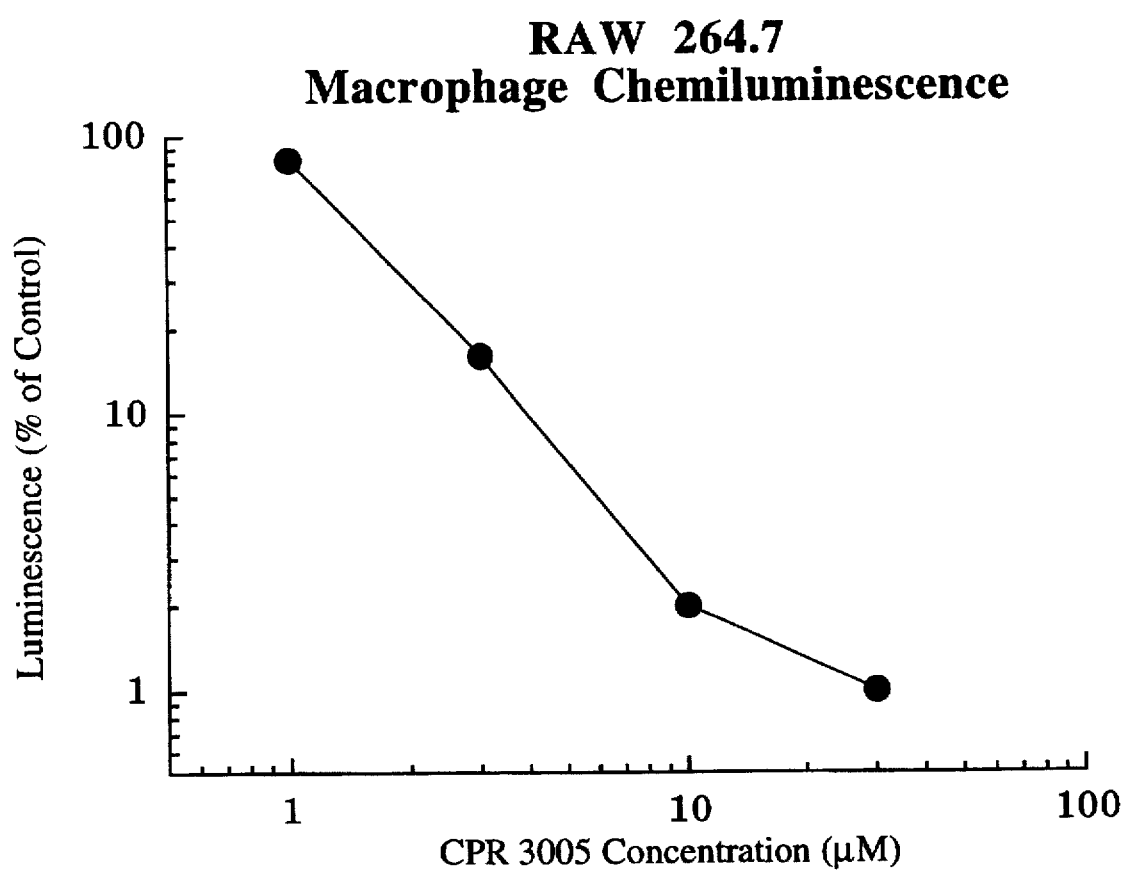
FIG. 4 is a graphical representation of results from an in vitro RAW 264.7 cell macrophage inhibition chemiluminescence assay of a compound of the invention, designated CPR 3005.

1. Cell line: RAW 264.7 (ATCC TIB 71);
2. Culture medium: DMEM with 10% FBS (attachment dependent);
3. Standard protocol for culturing cell lines: in T-75 or T-150 flasks; 37° C.; 95% air; 5% $CO_2$; 100% humidity;
4. Cell lines are passaged when approximately 80% confluent; with trypsin (1 mg/ml) and EDTA (1 ml EDTA in Ca-Mg free Hank's balanced salt solution); at a 1:4 to 1:5 split;
5. Trypsinize the cells and count with a hemocytometer;
6. Adjust concentration of cells to approximately 1,000,000 cells per ml;
7. Suspend cells in DMEM lacking phenol red and without FBS;
8. Pipette 1 ml into a standard luminometer cuvet (12× 75), commercially available from Analytical Luminescence Laboratories (San Diego, Calif.);
9. Add luminol to final concentration of 1 μM;
10. Add test compound at concentrations of 0, 1, 3, 10, or 30 μM;
11. Add 100 nanograms of phorbol myristate acetate (PMA);
12. Wait 1 minute and read photo counts (i.e., luminescence) on a Monolight 2010 luminometer available from Analytical Luminescence Laboratories;
13. The results are represented in FIG. 4, which illustrates the marked decrease in measured luminescence by the compound CPR 3005 tested at concentrations above 1 μM. Results are calculated as percent of control (no test compound present).

EXAMPLE 16

Assay for Anti-PAF Activity in Anesthetized Guinea Pigs

Guinea pigs of 650–1000 g were used in order to facilitate catheterization of the jugular vein and carotid artery. The guinea pigs were anesthetized with 35–45 mg/kg pentobarbital sodium. When or if the recordings described below were unstable, anesthetic additions were made during the course of the intervention. The cutdown was a ventral medial incision over the cervical area so that the trachea, jugular vein and carotid artery could be cannulated. The animals were immediately attached to a volume regulated Harvard® rodent respirator, Model 683, via a tracheostomy and the respirator was set at 60 respirations per minute and a volume of 8 ml/kg to maintain a normal arterial $P_{CO2}$ of approximately 40 mm Hg. Pancuronium bromide, a muscle relaxant, was then given intravenously at a dose of 0.2 mg/kg to prevent spontaneous breathing. A tube was connected to the respirator pump and the endotracheal catheter was attached to a pressure-transducing strain gauge and then to a 2-channel Gilson® physiological recorder. One channel of the recorder inscribed the pressure tracing from the airway; the second channel inscribed the pressure tracing from a similar strain gauge attached directly to a catheter inserted into the carotid artery. These two parameters were measured before and after each drug was given and at each increment in the dose response studies with each drug candidate and recorded. Total pulmonary resistance (TPR) was calculated as the difference between the expiratory pressure and inspiratory pressures with a constant volume.

After the anesthetic and muscle relaxant were given, the animal was allowed to stabilize. The airway was gently suctioned with a syringe and the lungs are briefly inflated by closing the expiratory port on the ventilator until the pressure was approximately three times resting pressure. When the pressure returned to a steady state, this TPR was considered control pressure. The dose-related increases or decreases were quantitated against these controls to determine the percent inhibition of PAF activity. Two doses of PAF were given as controls before the test compound was administered.

Figure 5:
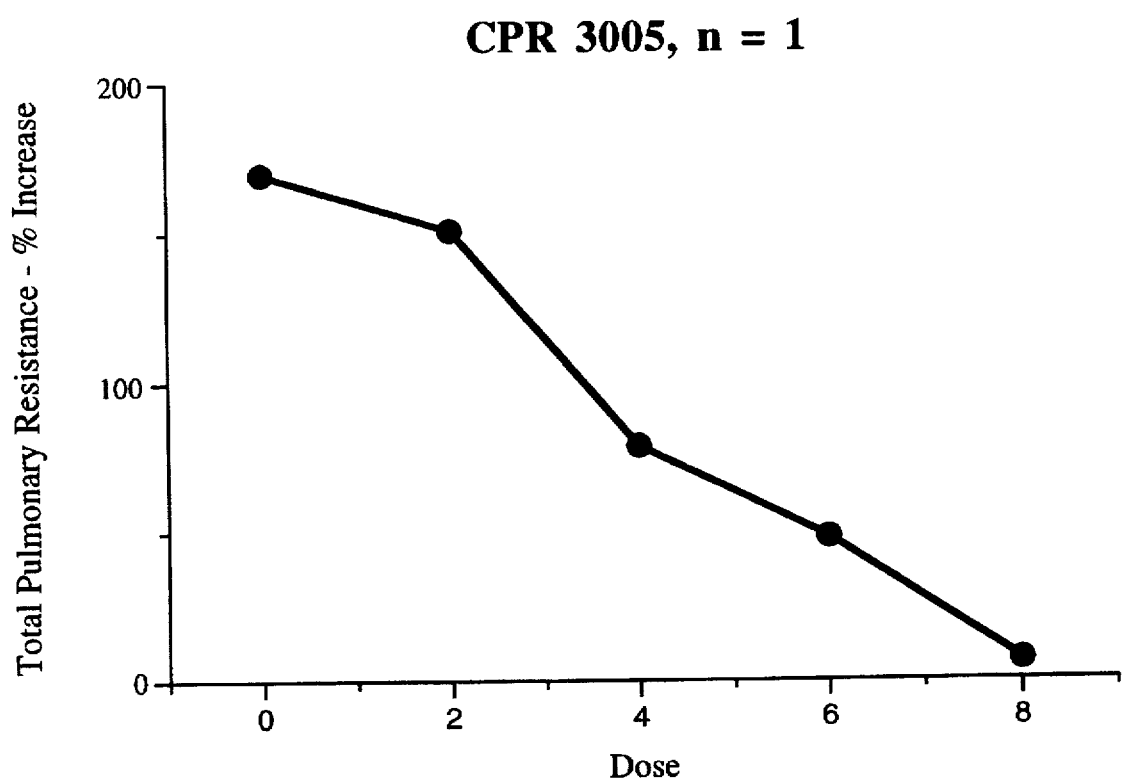
FIG. 5 is a graphical representation of results from an in vivo antagonism of PAF (Platelet Activating Factor)-induced increase in TPR (Total Pulmonary Resistance) by a compound of the invention, designated CPR 3005.

Incremental doses of 0.1, 1, and 10 μM of CPR 3005 change the PAF-induced increase in TPR in all animals as seen in FIG. 5. Decreases of TPR in a dose-related way indicate an inhibition of the constrictor activity of PAF on the airway.

EXAMPLE 17

Tablets

This is an illustrative example of tablets containing the following ingredients which may be prepared in a conventional manner:

| Ingredient | Per Tablet (mg) |
| --- | --- |
| CPR-3005 | 50–100 |
| Lactose | 70 |
| Maize starch | 70 |
| Polyvinylpyrrolidone | 5 |
| Magnesium stearate | 5 |
| Tablet weight | 200–250 |

EXAMPLE 18

Oil-in-Water Cream Base Formulation

This is an illustrative example of oil-in-water cream base formulation for topical use that may be prepared in a conventional manner:

| Ingredient | Weight (g) |
| --- | --- |
| CPR-3005 | 10.0 |
| Anhydrous lanolin | 20.0 |
| Polysorbate 60 | 4.0 |
| Sorbitan monopalmitate | 2.0 |
| Light liquid paraffin | 4.0 |
| Propylene glycol | 5.0 |
| Methyl hydroxybenzoate | 0.1 |
| Purified water to | 100.0 |

EXAMPLE 19

Capsules

This is an illustrative example of capsules containing the following ingredients which may be prepared in a conventional manner:

| Ingredient | Per Capsule (mg) |
|---|---|
| CPT 3005 | 50 |
| Lactose | 450 |
| Magnesium stearate | 5 |
| Capsule weight | 505 |

What is claimed is:

1. An N-Het-substituted glycerophosphoethanolamine of the formula:

$$\begin{array}{c} R-O-CH_2 \\ | \\ H_3C-O-CH \quad O \\ | \quad \| \\ H_2C-O-P-O-CH_2CH_2-{}^+NH_2-Het \\ | \\ O^- \end{array}$$

the isomeric forms thereof, and the pharmaceutically acceptable salts thereof and the isomeric forms; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and Het represents a 5- to 9-membered monocyclic or bicyclic fused ring system with 1 to 3 heteroatoms, each heteroatom selected from oxygen, sulfur and nitrogen, and provided that Het is not an imidazolinyl ring system.

2. A glycerophosphoethanolamine of claim 1 wherein R is $C_{16-18}$ alkyl or alkenyl.

3. A glycerophosphoethanolamine of claim 1 wherein Het is 2-thiazolinyl.

4. A glycerophosphoethanolamine of claim 1 wherein R is $C_{18}$ alkyl and Het is 2-thiazolinyl.

5. A method of inhibiting cell growth of a solid tumor in a mammal afflicted with same which comprises administering to said mammal an anti-tumor effective amount of an N-Het-substituted glycerophosphoethanolamine of the formula:

$$\begin{array}{c} R-O-CH_2 \\ | \\ H_3C-O-CH \quad O \\ | \quad \| \\ CH_2-O-P-O-CH_2CH_2-{}^+NH_2-Het \\ | \\ O^- \end{array}$$

an isomeric form thereof, or a pharmaceutically acceptable salt of either; wherein R represents a substituted or unsubstituted straight of branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and Het represents a 5- to 9-membered monocyclic or bicyclic fused ring system with 1 to 3 heteroatoms, each heteroatom selected from oxygen, sulfur and nitrogen, and provided that Het is not an imidazolinyl ring system.

6. A method of claim 5 wherein, in the glycerophosphoethanolamine, R is $C_{16-18}$ alkyl or alkenyl.

7. A method of claim 5 wherein, in the glycerophosphoethanolamine, Het is 2-thiazolinyl.

8. A method of claim 5 wherein, in the glycerophosphoethanolamine, R is $C_{18}$ alkyl and Het is 2-thiazolinyl.

9. A method of treating psoriasis in a mammal afflicted with same which comprises administering to said mammal an anti-psoriatic effective amount of an N-Het-substituted glycerophosphoethanolamine of the formula:

$$\begin{array}{c} R-O-CH_2 \\ | \\ H_3C-O-CH \quad O \\ | \quad \| \\ H_2C-O-P-O-CH_2CH_2-{}^+NH_2-Het \\ | \\ O^- \end{array}$$

an isomeric form thereof, or a pharmaceutically acceptable salt of either; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and Het represents a 5- to 9-membered monocyclic or bicyclic fused ring system with 1 to 3 heteroatoms, each heteroatom selected from oxygen, sulfur and nitrogen, and provided that Het is not an imidazolinyl ring system.

10. A method of claim 9 wherein, in the glycerophosphoethanolamine, R is $C_{16-18}$ alkyl or alkenyl.

11. A method of claim 9 wherein, in the glycerophosphoethanolamine, Het is 2-thiazolinyl.

12. A method of claim 9 wherein, in the glycerophosphoethanolamine, R is $C_{18}$ alkyl and Het is 2-thiazolinyl.

13. A method of treating inflammation in a mammal afflicted with same which comprises administering to said mammal an anti-inflammatory effective amount of an N-Het-substituted glycerophosphoethanolamine of the formula:

$$\begin{array}{c} R-O-CH_2 \\ | \\ H_3C-O-CH \quad O \\ | \quad \| \\ H_2C-O-P-O-CH_2CH_2-{}^+NH_2-Het \\ | \\ O^- \end{array}$$

an isomeric form thereof, or a pharmaceutically acceptable salt of either; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and Het represents a 5- to 9-membered monocyclic or bicyclic fused ring system with 1 to 3 heteroatoms, each heteroatom selected from oxygen, sulfur and nitrogen, and provided that Het is not an imidazolinyl ring system.

14. A method of claim 13 wherein, in the glycerophosphoethanolamine, R is $C_{16-18}$ alkyl or alkenyl.

15. A method of claim 13 wherein, in the glycerophosphoethanolamine, Het is 2-thiazolinyl.

16. A method of claim 13 wherein, in the glycerophosphoethanolamine, R is $C_{18}$ alkyl and Het is 2-thiazolinyl.

17. A method of inhibiting PAF activity in a host mammal having a PAF-induced pathophysiological condition comprising administering to said mammal an effective PAF antagonist amount of an N-Het-substituted glycerophosphoethanolamine of the formula:

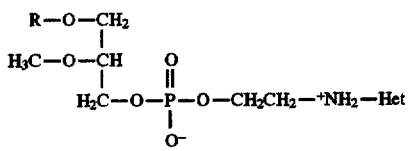

an isomeric form thereof, or a pharmaceutically acceptable salt of either; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and Het represents a 5- to 9-membered monocyclic or bicyclic fused ring system with 1 to 3 heteroatoms, each heteroatom selected from oxygen, sulfur and nitrogen, and provided that Het is not an imidazolinyl ring system.

18. A method of claim 17 wherein, in the glycerophosphoethanolamine, R is $C_{16-18}$ alkyl or alkenyl.

19. A method of claim 17 wherein, in the glycerophosphoethanolamine, Het is 2-thiazolinyl.

20. A method of claim 17 wherein, in the glycerophosphoethanolamine, R is $C_{18}$ alkyl and Het is 2-thiazolinyl.

21. A pharmaceutical composition comprising an effective anti-tumor, anti-psoriatic, anti-inflammatory or PAF antagonist amount of an N-Het-substituted glycerophosphoethanolamine of the formula:

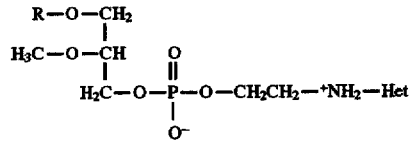

an isomeric form thereof, or a pharmaceutically acceptable salt of either; wherein R represents a substituted or unsubstituted straight or branched chain $C_{14-20}$ alkyl or alkenyl, said substituent being one or more of halo, $C_{1-3}$ alkoxy or cyano, provided that a double bond of said alkenyl does not involve the carbon atom of said alkenyl that is bonded to the oxygen of the glyceryl backbone; and Het represents a 5- to 9-membered monocyclic or bicyclic fused ring system with 1 to 3 heteroatoms, each heteroatom selected from oxygen, sulfur and nitrogen, and provided that Het is not an imidazolinyl ring system; and the pharmaceutically acceptable salts thereof; and a pharmaceutically acceptable carrier.

22. The composition of claim 21 wherein R is $C_{16-18}$ alkyl or alkenyl.

23. The composition of claim 21 wherein Het is 2-thiazolinyl.

24. The composition of claim 21 wherein R is $C_{18}$ alkyl and Het is 2-thiazolinyl.

25. The composition of claim 21 in unit dosage form as a tablet or capsule containing from about 0.5 to about 500 mg of said N-Het-Substituted glycerophosphethanolamine, isomeric form thereof or salt thereof.

26. The composition of claim 21 suitable for oral administration.

27. The composition of claim 21 suitable for parenteral administration.

28. The composition of claim 21 suitable for topical administration.

29. The composition of claim 21 suitable for inhalation administration.

* * * * *